(12) United States Patent
Noto (10) Patent No.: US 8,519,357 B2
(45) Date of Patent: Aug. 27, 2013

(54) CLEANING APPARATUS FOR SANITIZING FURNISHINGS

(76) Inventor: Anthony Peter Noto, Knightdale, NC (US)

( * ) Notice: Subject to any disclaimer, the term of this patent is extended or adjusted under 35 U.S.C. 154(b) by 440 days.

(21) Appl. No.: 12/909,214

(22) Filed: Oct. 21, 2010

(65) Prior Publication Data

US 2011/0095205 A1    Apr. 28, 2011

Related U.S. Application Data

(60) Provisional application No. 61/254,183, filed on Oct. 22, 2009, provisional application No. 61/254,193, filed on Oct. 22, 2009.

(51) Int. Cl.
*A61L 2/10* (2006.01)

(52) U.S. Cl.
CPC ............... *A61L 2/10* (2013.01); *A47L 2601/10* (2013.01)
USPC ........... 250/455.11; 422/24; 134/1; 134/25.4; 134/32; 226/176; 226/181

(58) Field of Classification Search
CPC .............................. A61L 2/10; A47L 2601/10
USPC ............ 250/453.11, 454.11, 455.11; 422/24; 134/15, 1, 25.4, 32; 226/176, 181; 271/272
See application file for complete search history.

(56) References Cited

U.S. PATENT DOCUMENTS

| | | | | |
|---|---|---|---|---|
| 4,029,251 A | * | 6/1977 | Johnson | 226/154 |
| 4,449,050 A | * | 5/1984 | Kamhi | 250/455.11 |
| 4,786,812 A | * | 11/1988 | Humphreys | 250/455.11 |
| 5,007,968 A | * | 4/1991 | Coffman et al. | 134/25.4 |
| 5,958,336 A | * | 9/1999 | Duarte | 422/24 |
| 7,040,613 B2 | * | 5/2006 | Vedoy | 271/10.07 |
| 2006/0216193 A1 | * | 9/2006 | Johnson et al. | 422/24 |

* cited by examiner

*Primary Examiner* — Jack Berman
(74) *Attorney, Agent, or Firm* — NK Patent Law, PLLC (57) ABSTRACT

A cleaning apparatus is provided. The apparatus includes a casing that defines an inlet opening on a first surface thereof and an outlet opening on a second surface thereof. An elongate path is formed therebetween for receiving an article to be cleaned. A sanitizing device is carried by the casing in proximity to the path for sanitizing the article to be cleaned. A first roller is carried by the casing and extends into the path. The first roller is configured to rotate in the direction of the path to thereby translate the article to be cleaned from the inlet opening to the outlet opening.

20 Claims, 7 Drawing Sheets

CLEANING APPARATUS FOR SANITIZING FURNISHINGS

CROSS REFERENCE TO RELATED APPLICATIONS

This application claims priority to U.S. Provisional Patent Application No. 61/254,183 filed on Oct. 22, 2009, and 61/254,193 filed on Oct. 22, 2009, the contents of both of which are hereby incorporated by reference.

TECHNICAL FIELD

The presently disclosed subject matter is directed towards a cleaning apparatus for sanitizing an article to be cleaned, and more particularly, towards a cleaning apparatus for sanitizing room furnishings such as bedding furniture using a sanitization device such as ultraviolet light.

BACKGROUND

In order to clean furnishings in places such as a private residence, hotel, or hospital, the covering articles are removed from the furnishings and are typically washed in a washing machine. This may be an effective manner in cleaning the covering articles, however, this does not effectively clean the underlying furnishings that those articles cover such a bed or pillow. The underlying furnishings are susceptible to bacteria, virus, mold, fungi, dust mites, fleas, lice, bed bugs, dead human skin, and other unwanted and potentially unsafe toxins, organisms, and human by-products.

The underlying furnishings are difficult to clean for several reasons. One such reason is that the unwanted and potentially unsafe toxins, organisms, and human by-products that may be found in underlying furnishings are not always effectively cleaned by traditional cleaning methods known in the art. For example, the bedding articles such as sheets or covers can be simply cleaned by soaking in a soap detergent solution. However, the underlying articles such as pillows or cushions cannot be easily cleaned in this manner because they are difficult to dry due to increased mass, water retention, and surface area. Additionally, no known portable device exists that can properly clean and sanitize these articles. The underlying articles could be vacuumed; however, this is a manual process and does not sanitize many of the microorganisms, toxins, and human by-products.

Devices incorporating ultraviolet light or steam have been developed to clean underlying furnishings. These devices are generally hand-held devices that must be manually scanned over the underlying furnishing. These devices suffer from a variety of disadvantages including that they are hand operated, are small in size and thus take substantial time to use, may expose the operator to ultraviolet light, don't effectively clean some microorganisms, toxins, and human by-products, and don't collect any of the dead matter or debris.

Accordingly, a need exists for a manner to clean underlying furnishings that addresses the various disadvantages associated with the prior art.

SUMMARY

This Summary is provided to introduce a selection of concepts in a simplified form that are further described below in the Detailed Description of Illustrative Embodiments. This Summary is not intended to identify key features or essential features of the claimed subject matter, nor is it intended to be used to limit the scope of the claimed subject matter.

Disclosed herein is a cleaning apparatus. The apparatus includes a casing defining an inlet opening on a first surface thereof and an outlet opening on a second surface thereof. An elongate path is defined between the inlet opening and outlet opening for receiving an article to be cleaned. A sanitizing device is carried by the casing in proximity to the path for sanitizing the article to be cleaned. A first roller is carried by the casing and extends into the path. The first roller is configured to rotate in the direction of the path to thereby translate the article to be cleaned from the inlet opening to the outlet opening.

According to another aspect, the first roller is selectively positionable to thereby adjust the distance that the roller extends into the path.

According to another aspect, a second roller extends into the path.

According to another aspect, the sanitizing device includes an ultraviolet light source for sanitizing the article to be cleaned.

According to another aspect, the light further includes a parabolic reflector for increasing the intensity of the light received on the article to be cleaned.

According to another aspect, the apparatus also includes guide bars positioned proximal the light for maintaining spacing between the light and the article to be cleaned.

According to another aspect, the sanitizing device includes a vacuum for sanitizing the article to be cleaned.

According to another aspect, a drive motor is coupled to the first roller for rotating the first roller.

According to another aspect, the sanitizing device includes a fluid spraying device for spraying fluids for sanitizing the article to be cleaned.

According to another aspect, a cleaning apparatus is provided. The apparatus includes a casing that defines an inlet opening on a first surface thereof and an outlet opening on a second surface thereof. The casing also defines an elongate path between the inlet opening and the outlet opening for receiving an article to be cleaned. A first roller is carried by the casing along the path and is configured to rotate in the direction of the path to thereby translate the article to be cleaned from the inlet opening through the path to the outlet opening. An ultraviolet light source is provided for sanitizing the article to be cleaned by eradicating foreign bodies treatable by ultraviolet light. The light source is positioned along the path and is downstream of the first roller. A vacuum may be provided for sanitizing the article to be cleaned by collecting the foreign bodies treatable by the ultraviolet light. The vacuum is positioned along the path and is downstream of the ultraviolet light source.

According to another aspect, the first roller, the ultraviolet light source, and the vacuum are selectively positionable to thereby adjust the distance that each of the first roller, the ultraviolet light source, and the vacuum extends into the path.

According to another aspect, a cleaning apparatus is provided. The apparatus includes a casing that defines an inlet opening on a first surface thereof and an outlet opening on an opposing second surface thereof. The casing further defines an elongate path between the inlet opening and the outlet opening for receiving an article to be cleaned. A frame support is positioned within the casing in proximity to the path and moveable in a generally orthogonal direction relative to the path. At least one roller is carried by the frame support and has a direction of rotation in the direction of the path to thereby translate the article to be cleaned from the inlet opening through the path to the outlet opening. At least one sanitizing device is carried by the frame support for sanitizing the article to be cleaned and is positioned downstream of the at least one roller.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed invention is not limited to the specific methods and instrumentalities disclosed. In the drawings.

DETAILED DESCRIPTION

The presently disclosed invention is described with specificity to meet statutory requirements. However, the description itself is not intended to limit the scope of this patent. Rather, the inventors have contemplated that the claimed invention might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Figure 1:
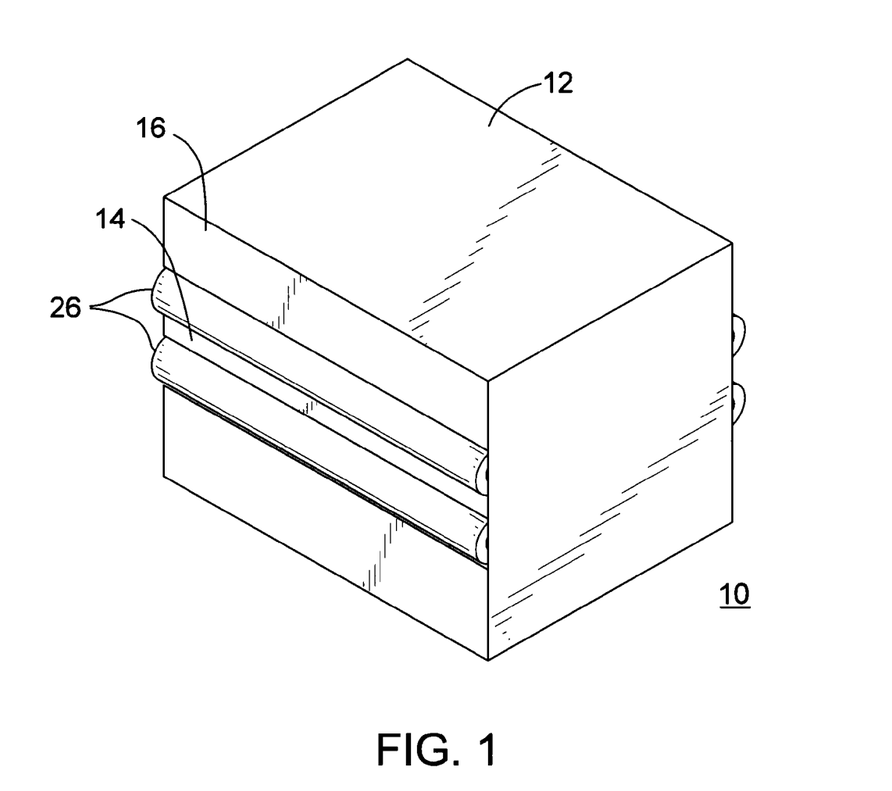
FIG. 1 is a perspective view of an apparatus for sanitizing articles to be cleaned.
Figure 2:
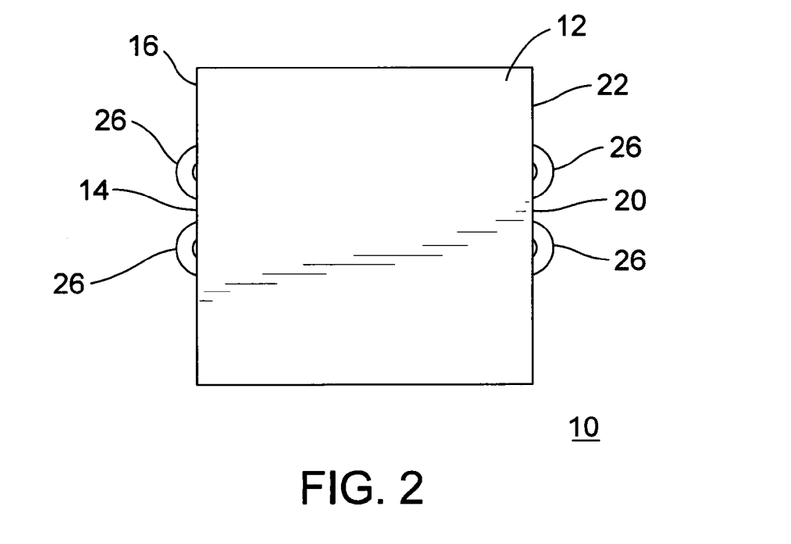
FIG. 2 is a side view of the apparatus for sanitizing articles to be cleaned.

A cleaning apparatus is depicted throughout the drawings and is generally designated as 10. As generally illustrated in FIGS. 1 and 2, the apparatus includes a casing 12 that may be made of any suitable material, and in one or more embodiments, may be made from lightweight materials such as plastic or aluminum. The casing 12 defines an inlet opening 14 on a first surface 16 thereof. Additionally, the casing 12 defines an outlet opening 20 on a second surface 22 thereof.

Figure 3:
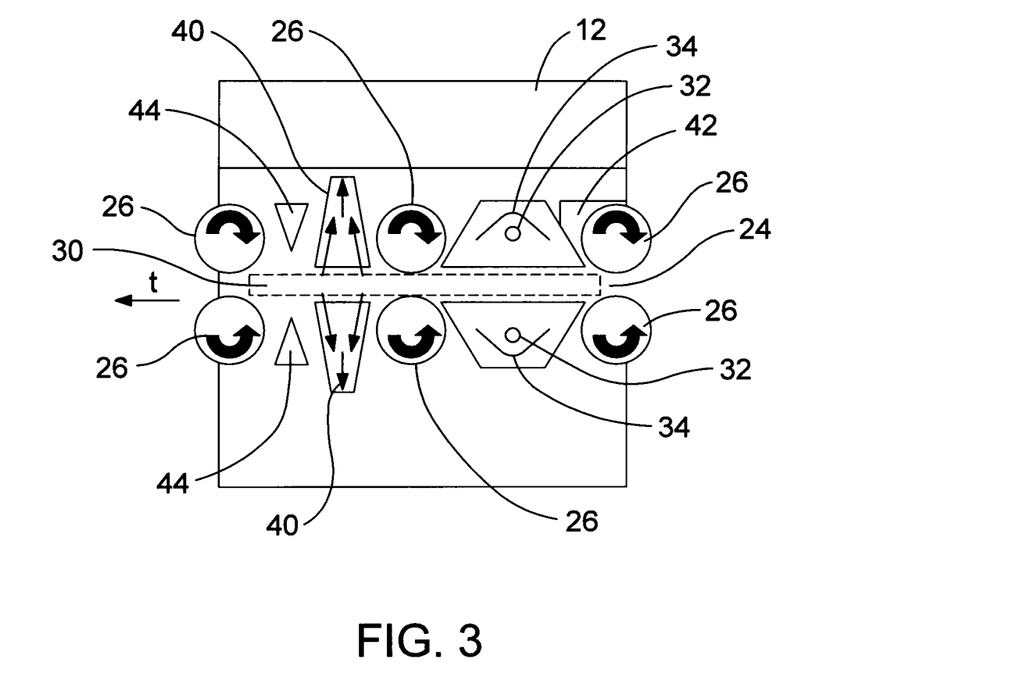
FIG. 3 is a side, cross-sectional view of the apparatus for sanitizing articles to be cleaned.

As illustrated in FIG. 3, an elongate path 24 is defined between the inlet opening 14 and the outlet opening 20 for receiving an article to be cleaned. As used herein, article to be cleaned is generally designated as 1 and may be any suitable article, including furnishings and the like. A pillow is shown throughout some of the drawings provided herein for illustrative, non-limiting purposes only.

As illustrated more clearly in FIG. 3, a sanitizing device is carried by the casing 12 in proximity to the path 24 for sanitizing the article to be cleaned. More particularly, the sanitizing device may be any device for sanitizing the article to be cleaned 1, and in one or more embodiments, may be an ultraviolet light source 32 for sanitizing the article to be cleaned. The light source 32 be any appropriate light source, and in one or more embodiments, may be an ultraviolet light such as UV-C. The ultraviolet light source 32 may include a parabolic reflector 34 for increasing the intensity of the light received on an article to be cleaned. Additional reflectors or lights 30 may be provided on the inner facing sides of the casing 12 for sanitizing the sides of the article to be cleaned 1.

The sanitizing device may also be a vacuum 40 for sanitizing the article to be cleaned 1. The vacuum 40 may be positioned downstream of the light source 32 in order to vacuum away any foreign bodies eradicated, killed, or destroyed by the light source 32. The vacuum 40 may have an internal vacuum pump carried within the casing 12 or may have an external vacuum pump that is sealably attached to the vacuum 40. Likewise, a vacuum tank may be carried within the casing 12 or may be provided at an external location for storing vacuumed substances.

The sanitizing device may also be a fluid spraying device 44 for spraying fluids for sanitizing the article to be cleaned 1. The fluid spraying device 44 may be provided for spraying steam, ozone, liquid, gas, or other chemicals for sanitizing or providing aromas to the article to be cleaned 1. In other embodiments, multiple spraying devices may be provided for spraying various chemicals or fluids.

At least one roller wheel 26 may be carried by the casing 12. The roller wheel 26 may extend into the path 24 for contacting the article to be cleaned 1. The roller wheel 26 is configured to rotate in the direction of the path 24 to thereby translate the article 1 from the inlet opening 14 to the outlet opening 20. Each of the at least one roller wheel 26 may be selectively positionable to thereby adjust the distance that the roller wheel 26 extends into the path 24. As illustrated in FIG. 3, multiple roller wheels 26 may be provided along the path 24. A drive motor 42 may also be coupled to one of, or any multiple of, the roller wheels 26 for imparting rotational movement thereto.

The various sanitizing devices and roller wheels 26 may be carried by a frame support 50. Frame support 50 may be coupled to the casing 12 by a spring 52, or may be coupled in any other appropriate manner. The frame support 50 is configured for generally orthogonal movement relative to the path 24 to thereby vary the distance that the roller wheels 26 extend in to the path 24. In this manner, the apparatus 10 is configured for fitting articles having variously sized heights and is automatically adjusting to those variously sized heights. The roller wheel 26 thus provides an interference contact with the article 1 and the rotation of the roller wheel 26 thus imparts translation of the article 1 along the path 24. A lever or other device may be coupled to the frame support 50 for adjusting the vertical spacing between roller wheels 26.

Figure 5:
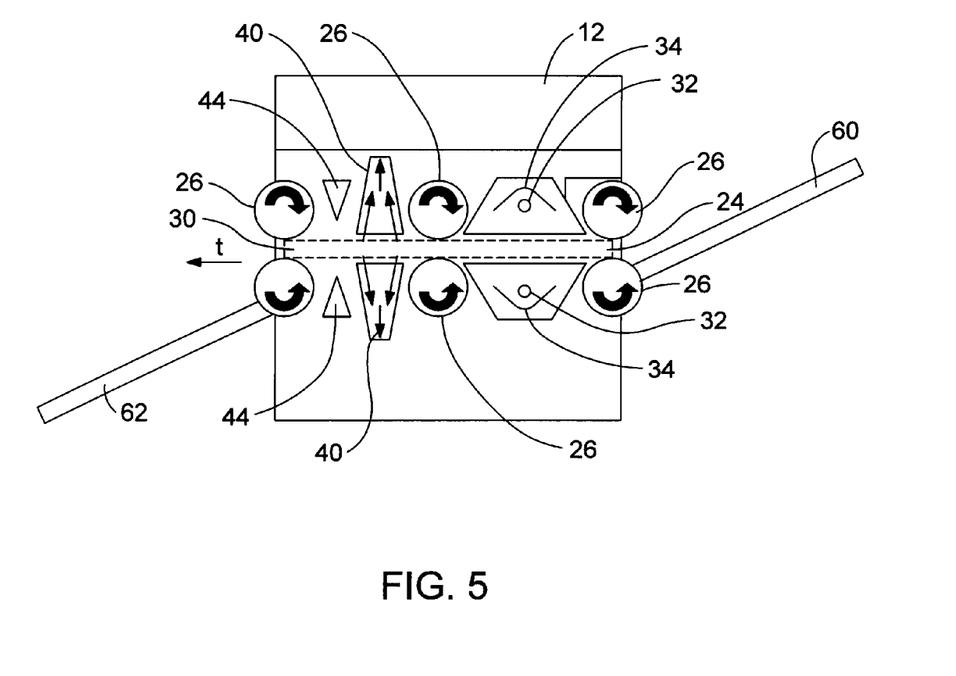
FIG. 5 is a side, cross-sectional view of the apparatus for sanitizing articles to be cleaned according to another embodiment.

As illustrated in FIG. 5, an inlet guide 60 may be provided at about the inlet opening 14 for positioning the article to be cleaned 1 for entry therein. Additionally, an outlet guide 60 may be provided at about the outlet opening 20 for positioning the article 1 after cleaning. Additionally, the apparatus 10 may include a set of retractable wheels on a bottom facing portion thereof for allowing rolling transport of the apparatus.

Figure 4A:
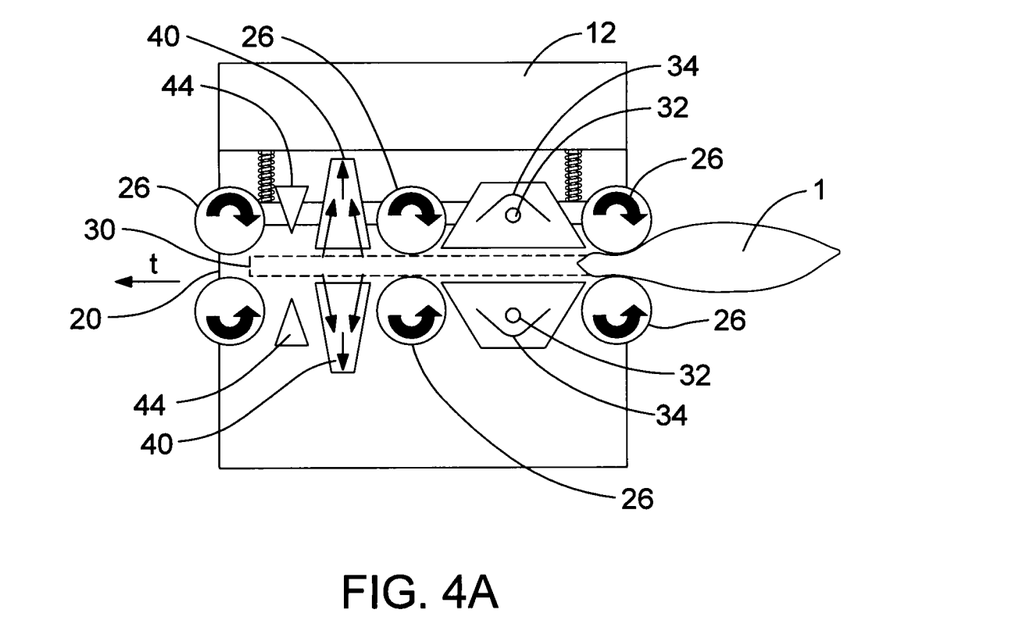
FIG. 4A is a side, cross-sectional view of an article to be cleaned positioned in an inlet opening of the apparatus.
Figure 4B:
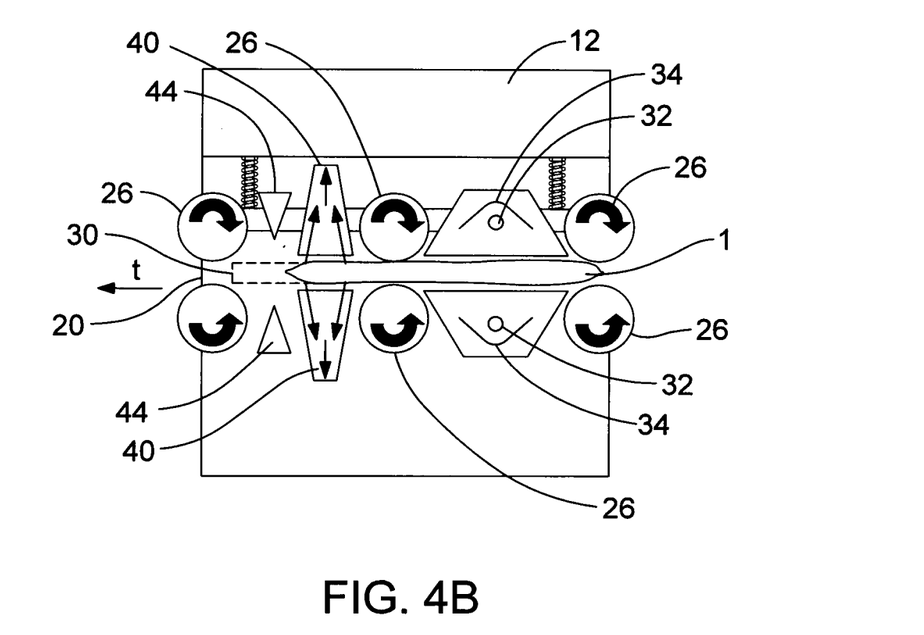
FIG. 4B is a cross-sectional view of an article to be cleaned positioned in a path of the apparatus.
Figure 4C:
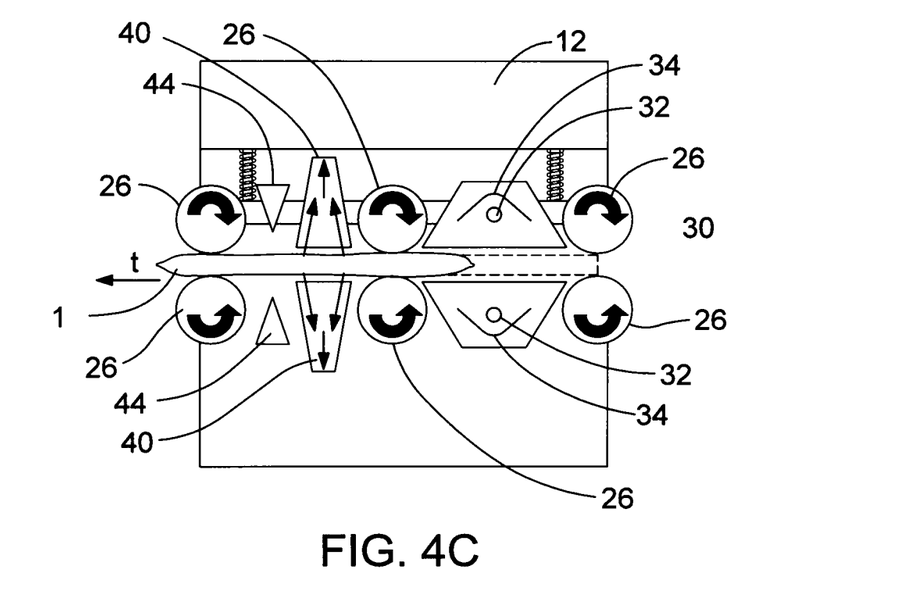
FIG. 4C is a side, cross-sectional view of an article to be cleaned positioned in a pathway and outlet opening of the apparatus.

A sequential illustration of operation of the apparatus 10 is depicted in FIGS. 4A, 4B, and 4C. As illustrated in FIG. 4A, the article to be cleaned 1 is positioned proximal the inlet opening 14 of the apparatus 10. The apparatus 10 is powered on and the roller wheel 26 imparts translational movement to the article 1 from the inlet opening 14 through the path 24 to the outlet opening 20 in the direction of arrow "t." The roller wheels 26 act to compress the article to be cleaned 1 so as to eliminate or reduce any non-orthogonal surfaces for more efficient and thorough sanitizing. As the article 1 translates through the path 24, the light source 32 eradicates foreign bodies that can be eradicated by ultraviolet light. A second set of roller wheels 26 positioned at a medial position along the path 24 may then contact the article 1 and provide additional translational forces thereto. At this point, the vacuum 40 may be aligned with the article 1 and begins vacuuming away debris. As the article 1 translates further along the path 24, the fluid spraying device 44 may then spray appropriate fluids to the article 1 for further sanitizing and/or aromatic refreshing. A third set of roller wheels 26 may then provide additional translational forces to the article 1 to translate the article 1 out of the outlet opening 20. A perturbator may also be provided about path 24 for providing mechanical agitation to the article to be cleaned 1.

Figure 6:
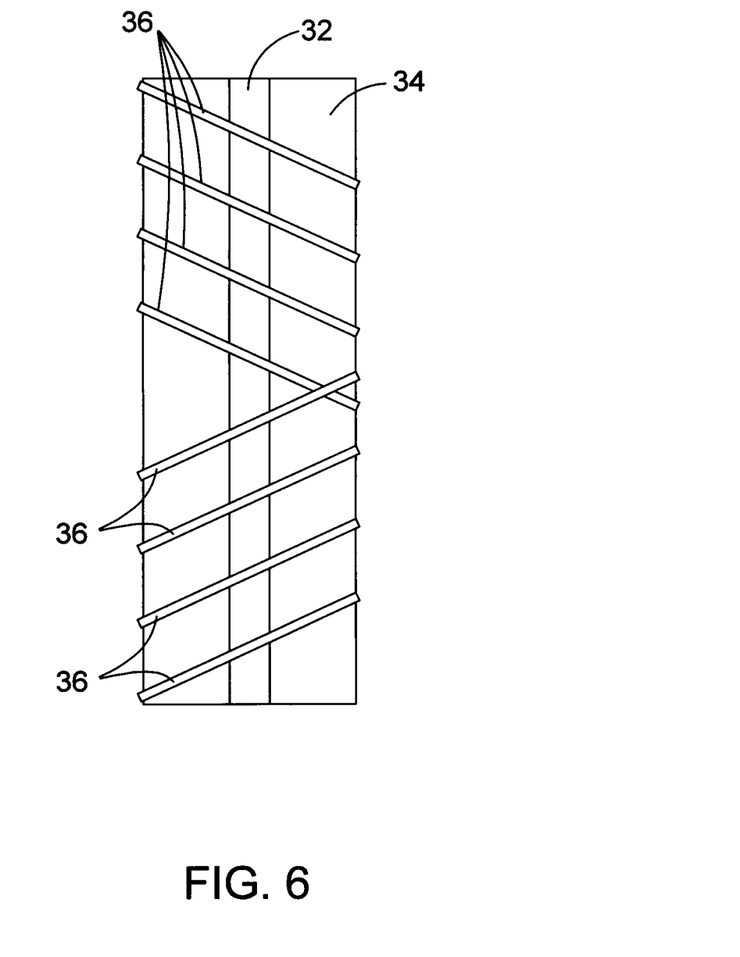
FIG. 6 is a bottom view of a sanitizing device for use with the cleaning apparatus, and more particularly, an ultraviolet light for sanitizing the article to be cleaned.

As illustrated in FIG. 6, the light 32 may further include a plurality of guide bars 36 for maintaining spacing between the light source 32 and the article to be cleaned 1. The guide bars 36 are arranged in generally spaced-apart arrangement and at an angle relative to the light 32 such that at some point during the scanning process, the article 1 will not be obstructed by the guide bars 36. In one or more alternate embodiments, a light transmissive panel may be used in lieu of the guide bars 36, and may be a TEFLON® panel.

Figure 7:
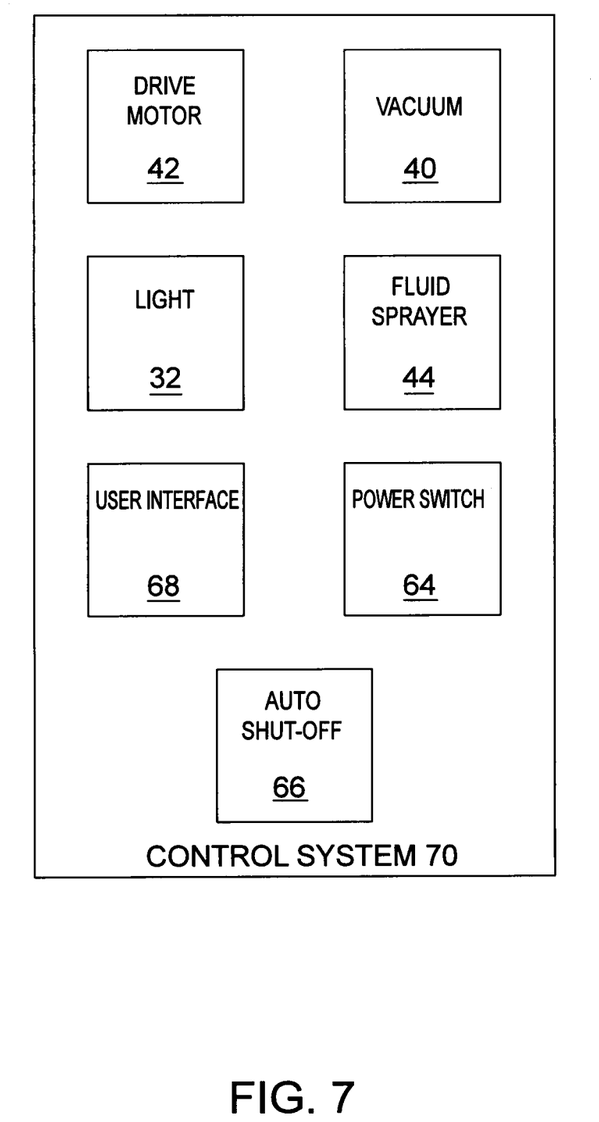
FIG. 7 is a schematic view of a control system for use with the cleaning apparatus.

The apparatus 10 includes a control system for providing control signals thereto. For example, as illustrated in FIG. 7, the control system 70 may be in communication with the light 32, vacuum 40, fluid spraying device 44, drive motor 42, an auto-shut off feature 66, a power switch 64 for powering on and off the apparatus 10, and a user interface 68. The vacuum pressure may be controlled or cycled to prevent collecting the item being cleaned. The auto-shut off feature 66 may be provided for detecting when the apparatus 10 has sanitized a respective article to be cleaned 1 or has been in operation for a predetermined period of time. In this manner, once the apparatus 10 has completed sanitizing the articles 1 or has been in operation for a predetermined period of time, the auto-shut off feature 66 may power off the apparatus, display a visual or audible indication of completion, or a combination thereof. The control system 70 may also be in communication with at least one safety switch to prevent accidental exposure to ultraviolet light or fluid spray from the light 32 and fluid spraying device 44, respectively.

The user interface 68 is provided for allowing the operator to select operating conditions for the apparatus 10. For example, the operator may desire that only the light 32 and vacuum 40 operation be conducted on the article to be cleaned 1. The user interface 68 allows the operator to select these desired operations and communicates those instructions to the control system 70. In another example, the operator may desire a longer cleaning cycle and select such a longer cleaning cycle on the user interface for communicating with the control system 70.

Figure 8:
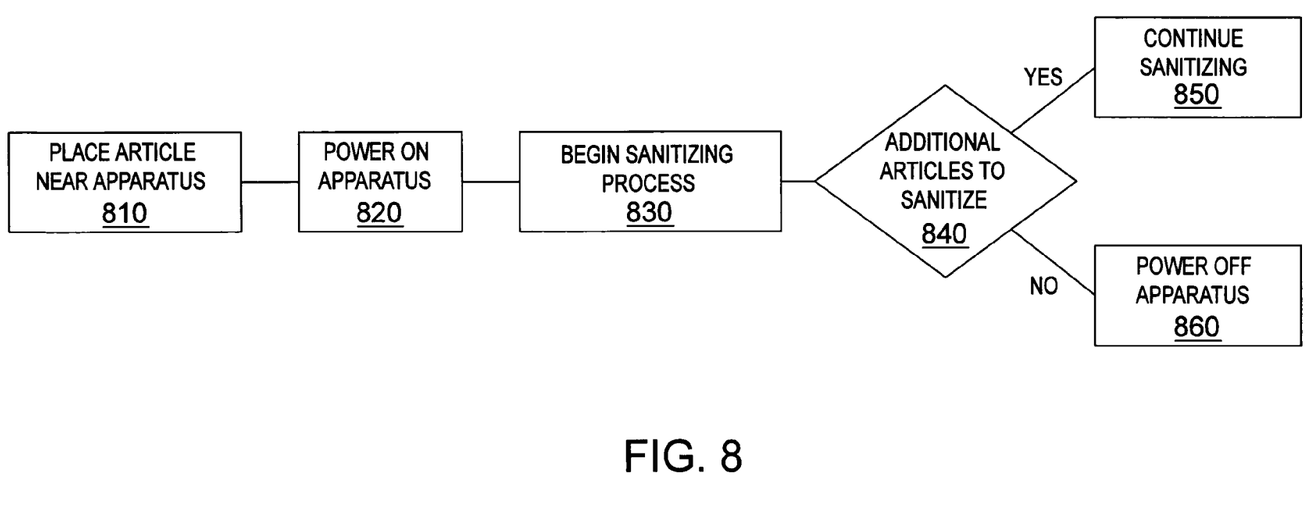
FIG. 8 is a flow chart depicting operation of the cleaning apparatus.

Operation and use of the apparatus 10 for sanitizing the article to be cleaned 1 is illustrated in the flow chart of FIG. 8. The operator places the article to be cleaned near the apparatus 810. The operator then powers on the apparatus 820, which may be done manually or by smart sensing technology when an article is placed near the apparatus. The apparatus then begins the sanitizing process 830. The apparatus or the operator then determines whether additional articles remain to be sanitized 850. If there are additional articles to be sanitized, the apparatus will continue sanitizing 850. If no additional articles remain to be sanitized, the apparatus is powered off 860.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A cleaning apparatus comprising:
a casing defining an inlet opening on a first surface thereof and an outlet opening on a second surface thereof and further defining an elongate path therebetween for receiving an article to be cleaned;
a sanitizing device carried by the casing in proximity to the path for sanitizing the article to be cleaned; and
a first roller carried by the casing and extending into the path, wherein the first roller is configured to rotate in the direction of the path to thereby translate the article to be cleaned from the inlet opening to the outlet opening, and wherein the first roller is actively positionable relative to the casing to adjust to the article to be cleaned.

2. The apparatus according to claim 1, wherein the first roller is selectively positionable to thereby adjust the distance that the roller extends into the path.

3. The apparatus according to claim 1, further including at least a second roller extending into the path on an opposing side of the path from the first roller.

4. The apparatus according to claim 1, wherein the sanitizing device comprises an ultraviolet light source for sanitizing the article to be cleaned.

5. The apparatus according to claim 4, wherein the light source further comprises a parabolic reflector for increasing the intensity of light received on the article to be cleaned.

6. The apparatus according to claim 5, further including guide bars positioned proximal the light source for maintaining spacing between the light source and the article to be cleaned.

7. The apparatus according to claim 1, wherein the sanitizing device comprises a vacuum for sanitizing the article to be cleaned.

8. The apparatus according to claim 1, further including a drive motor coupled to the first roller for rotating the first roller.

9. The apparatus according to claim 1, wherein the sanitizing device includes a fluid spraying device for spraying fluids for sanitizing the article to be cleaned.

10. A cleaning apparatus comprising:
a casing defining an inlet opening on a first surface thereof and an outlet opening on a second surface thereof and further defining an elongate path therebetween for receiving an article to be cleaned;
a first roller carried by the casing along the path and configured to rotate in the direction thereof to thereby translate the article to be cleaned from the inlet opening through the path to the outlet opening, wherein the first roller is actively positionable relative to the casing to adjust to the article to be cleaned;
an ultraviolet light source for sanitizing the article to be cleaned by eradicating foreign bodies treatable by ultraviolet light, the light source being positioned along the path and downstream of the first roller; and a vacuum for sanitizing the article to be cleaned by collecting the foreign bodies treatable by the ultraviolet light source, the vacuum being positioned along the path and downstream of the ultraviolet light source.

11. The apparatus according to claim 10, wherein the first roller, the ultraviolet light source, and the vacuum are selectively positionable to thereby adjust the distance that each of the first roller, the ultraviolet light source, and the vacuum extends into the path.

12. The apparatus according to claim 10, further including at least a second roller extending into the path.

13. The apparatus according to claim 10, wherein the light source further comprises a parabolic reflector for increasing the intensity of light received on the article to be cleaned.

14. The apparatus according to claim 13, further including guide bars positioned proximal the light source for maintaining spacing between the light source and the article to be cleaned.

15. The apparatus according to claim 10, further including a drive motor coupled to the first roller for rotating the first roller.

16. The apparatus according to claim 10, wherein the sanitizing device includes a fluid spraying device for spraying fluids for sanitizing the article to be cleaned.

17. A cleaning apparatus comprising:
a casing defining an inlet opening on a first surface thereof and an outlet opening on an opposing second surface thereof and further defining an elongate path therebetween for receiving an article to be cleaned;
a frame support positioned within the casing in proximity to the path and moveable in a generally orthogonal direction relative to the path;
at least one roller carried by the frame support and having a direction of rotation in the direction of the path to thereby translate the article to be cleaned from the inlet opening through the path to the outlet opening; and
at least one sanitizing device carried by the frame support for sanitizing the article to be cleaned, the sanitizing device being positioned downstream of the at least one roller.

18. The apparatus according to claim 17, further comprising a guide positioned at each of the inlet opening and outlet opening.

19. The apparatus according to claim 17, wherein the sanitizing device consists of an ultraviolet light source for sanitizing the article to be cleaned, a vacuum for sanitizing the article to be cleaned, a fluid dispensing device for spraying fluids for sanitizing the article to be cleaned, or a combination thereof.

20. A cleaning apparatus according to claim 17, wherein the at least one roller is actively positionable relative to the casing in the generally orthogonal direction relative to the path.

* * * * *